United States Patent [19]

Suzuki et al.

[11] Patent Number: 5,064,849

[45] Date of Patent: Nov. 12, 1991

[54] HETEROCYCLIC DERIVATIVES USEFUL AS RADIOSENSITIZING AGENTS AND ANTIVIRAL AGENTS

[75] Inventors: Toshimitsu Suzuki; Masakazu Sakaguchi; Yoshiyuki Miyata; Tomoyuki Mori, all of Yokohama, Japan

[73] Assignee: Pola Chemical Industries Inc., Shizuoka, Japan

[21] Appl. No.: 510,869

[22] Filed: Apr. 18, 1990

Related U.S. Application Data

[62] Division of Ser. No. 247,376, Sep. 21, 1988, Pat. No. 4,945,102.

[30] Foreign Application Priority Data

Oct. 22, 1987 [JP] Japan .................................. 62-267485

[51] Int. Cl.[5] ..................... A61K 31/41; C07D 249/14
[52] U.S. Cl. ................................. 514/383; 548/264.8; 424/1.1
[58] Field of Search ..................... 548/264.8; 514/383; 424/1.1

[56] References Cited

U.S. PATENT DOCUMENTS 4,820,844 4/1989 Kogiya et al. .................. 548/264.8

OTHER PUBLICATIONS

Takamura et al., "Polorographic Screening, Etc.", CA 110:208538d (1989).

Primary Examiner—Mary C. Lee
Assistant Examiner—Patricia L. Morris
Attorney, Agent, or Firm—Oblon, Spivak, McClelland, Maier & Neustadt, P.C.

[57] ABSTRACT

A novel heterocyclic derivative of formula (I):

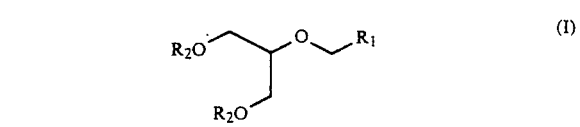

wherein $R_1$ represents

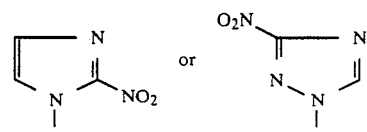

and $R_2$ represents hydrogen or acyl. When $R_2$ is acyl, the derivative can be prepared, for example, by the following process:

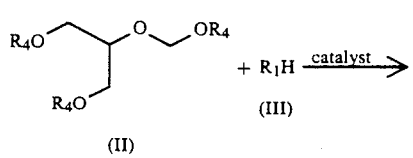

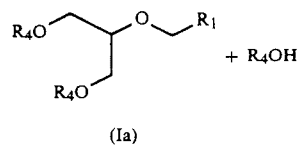

wherein $R_4$ is acyl and $R_1$ is

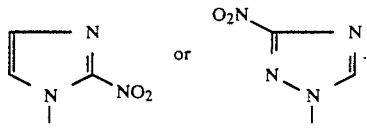

The derivative is less toxic and has radiosensitizing activity and antiviral activity even at a low concentration.

Radiosensitizing agents and antiviral agents containing the derivative as active component are also disclosed.

3 Claims, No Drawings

HETEROCYCLIC DERIVATIVES USEFUL AS RADIOSENSITIZING AGENTS AND ANTIVIRAL AGENTS

This is a division of application Ser. No. 247,376, filed on Sept. 21, 1988, now U.S. Pat. No. 4,945,102.

BACKGROUND OF THE INVENTION

1) Field of the Invention

This invention relates to a novel heterocyclic derivative of formula (I):

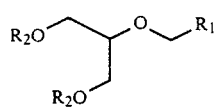

wherein $R_1$ represents

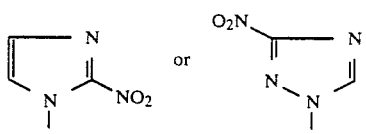

and $R_2$ represents a hydrogen atom or an acyl group; its preparation; and radiosensitizing agents and antiviral agents comprising the derivative as their active component.

2) Description of the Background Art

Hypoxic cells in tumor tissues are strongly resistant to radiation. This fact is considered to be one of key factors that explains the obstinacy or recrudescence after radiotherapy. In view that hypoxic cells do not exist in normal tissues, it is very important to enhance the radiosensitivity of the hypoxic cells in tumor tissues in order to obtain better results from radiotherapy.

Meanwhile, viral infectious diseases which attack mammals including humans are contagious and bring agony and economic loss to our society. Only limited viral infectious diseases are curable by currently available antiviral agents, and new synthetic antiviral agents stand in demand.

SUMMARY OF THE INVENTION

Under the above circumstances, the present inventors conducted intensive studies for developing agents capable of selectively sensitizing hypoxic cells without affecting the sensitivity of normal cells at the time of irradiation, in other words, radiosensitizing agents selectively directed to hypoxic cells (hereinafter referred to simply as radiosensitizing agents) and agents having antiviral activity. They found that compounds of formula (I) have low toxicity, high radiosensitizing effect, and antiviral activity even at a low concentration. The low toxicity of the compound is notable because toxicity has long been the most serious problem in this technical field.

Accordingly, it is an object of the invention to provide a heterocyclic derivative of formula (I) and a process for preparing the derivative. It is another object of the invention to provide a radiosensitizing agent and an antiviral agent comprising the derivative as their active component.

DETAILED DESCRIPTION OF THE INVENTION

When $R_2$ is acyl, compounds of formula (I) of this invention can be prepared, for example, by the following process:

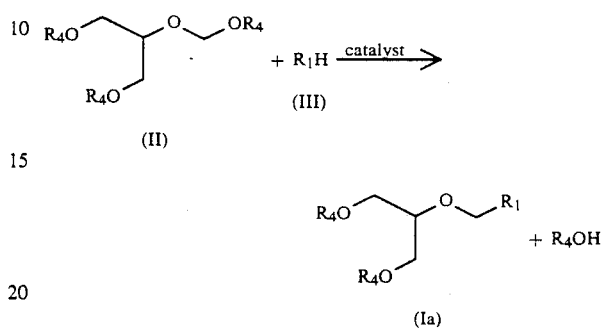

wherein $R_4$ represents an acyl group and $R_1$ has the same meaning as defined above.

In other words, compounds (Ia) of this invention can be prepared by reacting 1,3-diacyloxy-2-acyloxymethoxypropane (II) with a compound (III). The starting compound (II) is readily obtainable according, for example, to a method described in Proc. Nat. Acad. Sci. USA 80, 4139 (1983) by A. K. Fielol et al.

The above reaction is carried out by melting a compound (II) and a compound (III) under a reduced pressure in the presence of a catalyst. As suitable catalyst, mention may be made of: protic acids such as p-toluenesulfonic acid, methanesulfonic acid and trichloroacetic acid; and Lewis acids such as anhydrous zinc chloride, anhydrous aluminum chloride and anhydrous stannic chloride. The proportion of compound (II) and compound (III) may be varied arbitrarily. Generally, it is recommended that the compound (II) be used in equivalent or a little excessive amount. The reaction temperature is preferably from 50° to 150° C. The reaction is preferably completed in between 30 minutes to 6 hours, depending on reagent, solvent, temperature, reaction accelerator, etc.

The compounds (Ia) of this invention can also be prepared according to the following process:

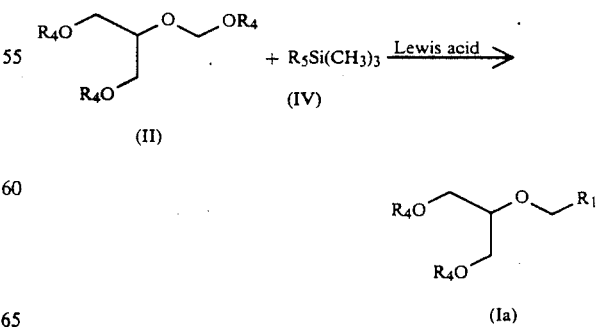

wherein $R_4$ as same as defined above and $R_5$ represents

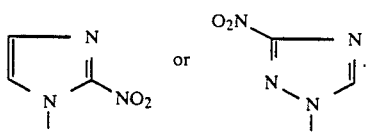

In other words, compounds (Ia) of this invention can be obtained by reacting 1,3-diacyloxy-2-acyloxymethoxypropane (II) with compound (IV) which is sililated derivative of compound (III).

The compounds (IV) are readily obtainable by reacting their corresponding compounds (III) with excessive amounts of N,O-bis(trimethylsilyl)acetamide at room temperature or under heat while stirring. Unreacted silylation agents are removed by distillation under reduced pressure.

The reaction process according to this invention is carried out in the presence of a Lewis acid. Various Lewis acids are usable, and specific examples include anhydrous stannic chloride, anhydrous aluminum chloride, anhydrous zinc chloride, etc. They are preferably used in a catalytic amount or equivalent amount of compound (II).

The proportion of compound (II) and compound (IV) may be varied arbitrarily. In general, it is recommended that the compound (II) be used in an equimolar or a slightly excessive amount with respect to compound (IV). Various solvents can be used in this reaction, which include acetonitrile, methylene chloride, benzene, toluene, etc. The reaction proceeds at temperatures ranging from −30° to +50° C., and generally under water cooling conditions or at room temperature. The reaction is preferably completed in between 30 minutes to 6 hours, depending on reagent, solvent, temperature, reaction accelerator, etc.

After the reaction is completed, the objective products are separated from the reaction mixture and purified according to a conventional method. For instance, the reaction mixture is subjected to extraction process, followed by condensation after washing the extract, and the residue being purified by chromatography to obtain a compound (Ia) at a high yield.

Going back to the general formula (I), compounds (I) having hydrogen as $R_2$ can be prepared by deacylation of compounds (Ia) as shown below:

One example of the deacylation process is such that proceeds in absolute alcohol containing sodium alcoholate or in absolute alcohol saturated with ammonia, at a temperature ranging from 0° C. to room temperature over a few hours to overnight. Another example of suitable deacylation is hydrolysis in water-alcohol using an organic base such as triethylamine, pyridine, etc. at a temperature ranging from room temperature to 80° C. As suitable alcohol, lower alcohols such as methanol, ethanol and propanol may be mentioned.

Examples of the novel compounds (I) of this invention are:

(1) 1-[2-acetoxy-1-(acetoxymethyl)ethoxy]methyl-2-nitroimidazol,
(2) 1-[2-acetoxy-1-(acetoxymethyl)ethoxy]methyl-3-nitro-1,2,4-triazol,
(3) 1-[2-hydroxy-1-(hydroxymethyl)ethoxy]methyl-2-nitroimidazol,
(4) 1-[2-hydroxy-1-(hydroxymethyl)ethoxy]methyl-3-nitro-1,2,4-triazol.

In this specification, the above compounds (1) to (4) will hereinafter be referred to as compound (1), compound (2), compound (3) and compound (4).

Compounds (I) of this invention have low toxicity as shown by the test below, and have excellent radio-sensitizing ability as well as antiviral activity. They are preferably dosed 5 minutes to 5 hours prior to irradiation either orally or non-orally. They may be formed into tablets, capsules, granules, powders, sapositories or injections together with excipients, stabilizers, preservatives, modifiers, etc. as required. The administration amount depends on the patient's age, the region where tumor is produced, species and types of tumor, conditions of the patient, etc., and is preferably 0.2 to 5.0 g/m² body surface.

Action and Effect

Acute toxicity test and other tests regarding radiosensitising ability and antiviral activity were carried out using the compounds of the present invention.

(1) Acute toxicity test

ICR strain male mice of 5 week old were intravenously or intraperitoneally administered with various compounds each dissolved in a physiological saline or in a physiological saline containing 10% DMSO. The mice were observed over 14 days and 50% death rates (LD$_{50/14}$) were obtained. The results are shown in Table 1.

TABLE 1

| Compound Nos. | Administration | Dose (mg/kg) | Dead/Treated | LD$_{50/14}$ | General Status |
|---|---|---|---|---|---|
| 1 | intraperitoneal | 720 | 0/2 | >860 | Clamed down |
|   | " | 860 | 0/2 |   |   |
| 2 | intraperitoneal | 600 | 0/2 | 790 | Transient respiratory acceleration after administration, then calmed down |
|   | " | 720 | 0/2 |   |   |
|   | " | 860 | 2/2 |   |   |
| 3 | intravenous | 720 | 0/2 | >860 | Calmed down |
|   | " | 860 | 0/2 |   |   |
| 4 | intravenous | 720 | 0/2 | 860 | Calmed down |
|   | " | 860 | 1/2 |   |   |

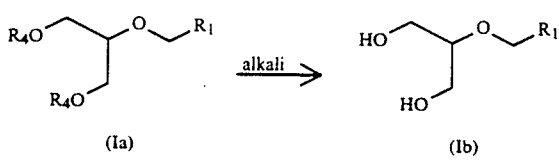

(2) Radiosensitivity test (a) In vitro test 1
Cells used in the test: single cells of EMT-6
Irradiation: $^{60}$Co - gamma rays
Cell treatment to hypoxia:
  A mixture gas of 95% nitrogen and 5% carbon dioxide was passed through cell suspension.
Survival ratio of cells:

Determined by counting colonies.
Radiosensitivity enhancement ratio (ER):

$$ER = \frac{\text{Required dose for obtaining a certain biological effect in non-administered group}}{\text{Required dose in administered group for obtaining the same biological effect as obtained in non-administered group}}$$

The results of this test are shown in Table 2.

TABLE 2

| Compound Nos. | Concentration (mM) | ER |
|---|---|---|
| 3 | 1.0 | 1.70 |
| 4 | 1.0 | 1.50 |

(b) In vitro test 2
Cells used in the test: Spheroids of EMT-6
Irradiation: $^{60}$Co - gamma rays
Tested compound: Compound (3), 1 mM
Determination of radiosensitivity enhancement:
  Six particles of spheroid having a certain size were taken and placed in a culture solution containing compound 3) having a concentration of 1 mM, and incubated at 37° C. over 30 to 60 minutes, followed by irradiation. The spheroids were treated by trypsin and then the enhancement ratio (ER) was obtained by counting colonies.
The result obtained was: ER of compound (3) at a concentration of 1 mM = 1.55
(c) In vivo test
Animal: Balb/c mice
Tumor: EMT-6
Tested compound: compound (3), 200 mg/kg
Administration:
  Compound (3) dissolved in a physiological saline was intraperitoneally administered 20 minutes prior to irradiation.
Irradiation: $^{60}$Co - gamma rays,
  whole body irradiation,
Determination of radiosensitivity enhancement:
  Enhancement ratio (ER) was obtained from irradiation dose and reduction ratio of tumor cells.
The result obtained was: ER of compound (3) (200 mg/kg) = 1.55
(3) Antiviral activity test
Virus: Herpes simplex virus type I
Cells: Vero (monkey kidney cells)
Culture medium: 2% FBS MEM
  A sample conditioned to contain $2 \times 10^5$/ml of vero cells was cultured at 37° C. in an atmosphere of 5% $CO_2$ for 1 day to obtain a monolayer sample. The sample was infected by HSV virus diluted with PBS (phosphate buffer). Compound (I) was dissolved in DMSO, then adjusted to have concentrations of 100 µg/ml, 50 µg/ml, 10 µg/ml, 5 µg/ml and 1 µg/ml by 2% FBS MEM, and served as test agents. The culture cells were added with each agent separately and incubated at 37° C. in a $CO_2$ incubator for one day. The cytopathic effect was observed under microscope. Cells were stained by crystal violet and scored as follows:
  0: almost all cells are dead
  1: certain effect of the agent with some dead cells
  2: normal
The results are shown in Table 3.

TABLE 3

| Compound Nos. | 100 µg/ml | 50 µg/ml | 10 µg/ml | 5 µg/ml | 1 µg/ml |
|---|---|---|---|---|---|
| 3 | 2 | 2 | 1 | 0 | 0 |
| 4 | 2 | 2 | 1 | 0 | 0 |

EXAMPLES

This invention may be more fully understood from the following examples.

EXAMPLE 1

1-[2-acetoxy-1-(acetoxymethyl)ethoxy]methyl-2-nitroimidazol: compound (1)

5.6 g of 2-nitroimidazol, 12.4 g of 1,3-diacetoxy-2-acetoxymethoxypropane and 0.5 g of p-toluenesulfonic acid monohydrate were placed in a flask connected with a trap for reducing pressure by an aspirator. The flask was heated by oil bath of 130°-140° C. under reduced pressure while stirred. Acetic acid was distilled out as the reaction proceeded. In about 15 minutes, the reaction was completed. After cooling down to room temperature, the content was added with about 300 ml ethyl acetate and subjected to extraction. The extract was washed with saturated aqueous sodium hydrogen carbonate, and with water in this order. Then it was dried over anhydrous sodium sulfate and concentrated under reduced pressure. The residue was purified by separable high performance liquid chromatography through silica gel columns using a mixture solvent (ethyl acetate - benzene) as an eluate to obtain 13.3 g of the title compound as a viscous oil material (yield: 88.6%).

MS(m/e): 301(M+)
IR(cm$^{-1}$): 1740 (CO), 1535 (NO$_2$), 1490 (NO$_2$)
NMR($\delta$, CDCl$_3$) 2.0 (s, 6H, CH$_3$CO x 2), 3.8–4.3 (m, 5H, —CH$_2$OAc x 2, >CH—), 5.9 (s, 2H, —OCH$_2$N<), 7.1 (s, 1H, ring proton), 7.4 (s, 1H, ring proton)

EXAMPLE 2

1-[2-acetoxy-1-(acetoxymethyl)ethoxy]methyl-3-nitro-1,2,4-triazol: compound (2)

General procedures of Example 1 were followed to obtain the title compound as a viscous oil material (yield: about 83%).

MS(m/e): 302(M+)
IR(cm$^{-1}$) 1740 (CO), 1555 (NO$_2$), 1500 (NO$_2$),
NMR($\delta$, CDCl$_3$): 2.0(s, 6H, CH$_3$CO x 2), 3.8–4.3 (m, 5H, —CH$_2$OAc x 2, >CH—), 5.9 (s, 2H, —OCH$_2$N>), 8.7 (s, 1H, ring proton)

EXAMPLE 3

1-[2-hydroxy-1-(hydroxymethyl)ethoxy]methyl-2-nitroimidazol: compound (3)

3.01 g of 1-[2-acetoxy-1-(acetoxynethyl)ethoxy]-methyl-2-nitroimidazol (compound (1)) was dissolved in 50 ml of absolute methanol, and stirred at room temperature while being added with 5% absolute ethanol solution of sodium ethoxide dropwise until pH reached 9.0. Stirred at room temperature over 3 hours. Then Dowex 50 W (H+, made by Dow Chemical) was slowly added until the liquid had a pH of 7.0. Dowex 50 W was removed by suction filtration, and the solvent was distilled off under reduced pressure. The residue was subjected to recrystallization by ethanol to obtain 2.83 g of the title compound as light yellow needles (yield: 94%).

Melting point: 88° C.
MS(m/e): 218 (M+1), 185, 114, 98
IR(cm$^{-1}$): 3450 (OH), 1540 (NO$_2$), 1490 (NO$_2$)
NMR [δ, DMSO(d$_6$)]: 3.2-3.6 (m, 5H, —C$\underline{H}_2$OH x 2, >C$\underline{H}$—), 4.6 (t, 2H, O$\underline{H}$x 2), 5.9(s, 2H, —OC$\underline{H}_2$N>), 7.15(s, 1H, ring proton), 7.8 (s, 1H, ring proton)

EXAMPLE 4

1-[2-hydroxy-1-(hydroxymethyl)ethoxy]methyl-3-nitro-1,2,4-triazol: compound (4)

General procedures of Example 3 were followed to obtain the title compound as colorless needles (yield: 95%).

Melting point: 132° C.
MS(m/e): 219 (M+1), 205, 185
IR(cm$^{-1}$): 3450 (OH), 1560 NO$_2$), 1500 (NO$_2$)
NMR[δ, DMSO(d$_6$)]: 3.3-3.8 (m, 5H, —C$\underline{H}_2$OH x 2, >C$\underline{H}$—), 4.6 (t, 2H, O$\underline{H}$x 2), 5.8 (s, 2H, —OC$\underline{H}_2$N>), 9.0 s, 1H, H in 5th position)

What is claimed is:

1. A heterocyclic derivative of the following formula (I):

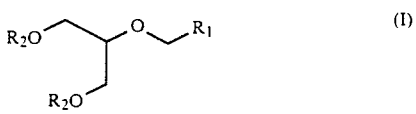

wherein R$_1$ represents

and R$_2$ represents a hydrogen atom or an acetyl group.

2. A radiosensitizing composition comprising as its active component a radiosensitizing effective amount of a heterocyclic derivative of formula I:

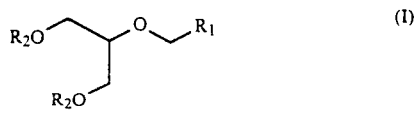

wherein R$_1$ represents

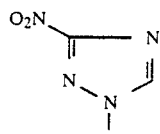

and R$_2$ represents a hydrogen atom or an acetyl group.

3. An antiviral composition comprising as its active component an antiviral effective amount of a heterocyclic derivative of the formula (I):

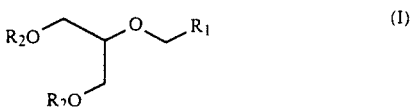

wherein R$_1$ represents

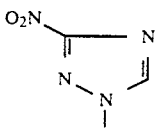

and R$_2$ represents a hydrogen atom or an acetyl group.

* * * * *